United States Patent [19]

Muntz et al.

[11] 4,014,911

[45] Mar. 29, 1977

[54] METHOD FOR PREPARING ETHYL VANADATE

[75] Inventors: Ronald L. Muntz, Bedford Hills, N.Y.; Robert W. Lerner, Trumbull, Conn.

[73] Assignee: Stauffer Chemical Company, Adrian, Mich.

[22] Filed: Oct. 16, 1975

[21] Appl. No.: 623,170

[52] U.S. Cl. .......................................... 260/429 R
[51] Int. Cl.² ........................................ C07F 9/00
[58] Field of Search ............ 260/429 R; 252/431 R

[56] References Cited

UNITED STATES PATENTS

| | | | |
|---|---|---|---|
| 3,652,617 | 3/1972 | Termin et al. | 260/429 R |
| 3,657,295 | 4/1972 | McCoy | 260/429 R |
| 3,772,355 | 11/1973 | Merz | 260/429 R |

*Primary Examiner*—Helen M. S. Sneed

[57] ABSTRACT

An improved method for preparing ethyl vanadate by reacting vanadium oxytrichloride with ethanol in the presence of ammonia and a hydrocarbon solvent and thereafter adding an amide which forms two liquid phases, one phase containing the ethyl vanadate and the other containing the undissolved ammonium chloride.

5 Claims, No Drawings

METHOD FOR PREPARING ETHYL VANADATE

This invention relates to ethyl vanadate and more particularly to a method for preparing ethyl vanadate.

Many methods have been proposed and employed for the preparation of ethyl vanadate. One method among such known methods involved reacting vanadium pentoxide with ethyl alcohol to form ethyl vanadate and water as a by-product, which was then removed as an azeotrope with the excess alcohol. One disadvantage of this method was that it required prolonged heating and caused degradation of the ethyl vanadate. Also, vanadium oxytrichloride has been reacted with an excess of butyl alcohol in the presence of ammonia to form butyl vanadate and ammonium chloride. The butyl vanadate solution was separated from the ammonium chloride crystals by filtration. However, since the small crystals of ammonium chloride have a tendency to plug up the filter, it was difficult to filter off the butyl vanadate solution. Moreover, the filtration step must be conducted in a closed system to prevent hydrolysis of the vanadate, thus resulting in an expensive process.

Also, butyl vanadate was prepared by reacting vanadium oxytrichloride with butyl alcohol in the presence of formamide saturated with ammonia. Two liquid layers were formed, one containing the butyl vanadate layer and the other containing the formamide-ammonium chloride by-product.

Surprisingly, it was found that when ethyl vanadate was prepared by this process, the reaction products did not form two phases. Thus, the ethyl vanadate must be separated from the ammonium chloride by filtration, which resulted in a substantial loss of material due to the absorptive characteristics of the ammonium chloride crystals.

It is therefore an object of the present invention to provide an improved method for preparing ethyl vanadate. Another object of this invention is to provide an improved method for separating ethyl vanadate from ammonium chloride crystals. A further object of this invention is to provide an improved method for preparing substantially pure ethyl vanadate.

The foregoing objects and others, which will become apparent from the following description, are accomplished in accordance with this invention, generally speaking, by providing an improved method for preparing ethyl vanadate by reacting vanadium oxytrichloride with ethanol in the presence of a hydrocarbon solvent and ammonia, to form ethyl vanadate and ammonium chloride, adding an amide selected from the class consisting of formamide or methyl formamide to form two liquid layers, one layer containing the ethyl vanadate hydrocarbon solvent and the other containing the ammonium chloride-amide suspension. The ethyl vanadate is then readily separated from the ammonium chloride-amide layer by any conventional technique known in the art.

Unexpectedly, it was found that ethyl vanadate will not form a separate phase when vanadium oxytrichloride is reacted with ethanol in the presence of ammonia and formamide. Even the addition of a hydrocarbon solvent will not enhance the separation of the ethyl vanadate from the ammonium chloride-amide solution. However, when the vanadium oxytrichloride is reacted with ethanol in the presence of ammonia and a hydrocarbon solvent and upon completion of the reaction, formamide or methyl formamide is added, the ethyl vanadate readily separates from the ammonium chloride-amide solution.

Examples of suitable amides which may be employed in this invention are formamide and methyl formamide.

The overall reaction between vanadium oxytrichloride and ethanol may be illustrated by the following equations.

$$VOCl_3 + C_2H_5OH \rightarrow C_2H_5OVOCl_2 + HCl$$

$$C_2H_5OVOCl_2 + 2C_2H_5OH + 2NH_3 \rightarrow (C_2H_5O)_3VO + 2NH_4Cl$$

Generally, vanadium oxytrichloride is admixed with ethanol and a hydrocarbon solvent and ammonia gas is bubbled through the reaction mixture. When vanadium oxytrichloride is added to ethanol, an exothermic reaction takes place and releases a quantity of hydrogen chloride. Some of the liberated hydrogen chloride may be removed prior to the addition of ammonia in order to reduce the formation of ammonium chloride by-product. This may be accomplished by passing a stream of an inert gas, e.g. krypton, xenon, radon, argon, helium, nitrogen or carbon dioxide through the reaction mixture to sweep out a portion of the hydrogen chloride released. Upon completion of the reaction, the amide is added to the reaction mixture, thereby resulting in the formation of two liquid phases, one being the ethyl vanadate and the other being the amide-ammonium chloride suspension. The vanadate product may be separated by decantation or any other conventional technique known in the art.

The vanadium oxytrichloride and ethanol are preferably employed in a mole ratio of about 1:3; however, they may be employed in a mole ratio of from 1:1 to 1:6. Where the mole ratio of vanadium oxytrichloride to ethanol is less than 1:3, the resulting product will consist of an ethyl substituted vanadium oxychloride.

Any hydrocarbon solvent which is immiscible with the amide and is not a solvent for ammonium chloride may be used in the process of this invention. Moreover, it is preferred that the ethyl vanadate be soluble in the hydrocarbon solvents. Preferably the hydrocarbon solvents are inert aliphatic or aromatic hydrocarbons such as pentane, hexane, octane, decane, dodecane, benzene, toluene, xylene and the like. A mixture of solvents may be employed, if desired.

Although the amount of hydrocarbon solvent present during the reaction is not critical, a sufficient amount should be present to form a polar layer and a nonpolar layer. Generally, the amount of hydrocarbon solvent should be in a weight ratio of solvent to vanadium oxytrichloride of from about 1:1 to about 5:1 and more preferably from about 2:1 to 4:1. The upper limit is primarily dependent on economic considerations.

It is preferred that some of the hydrogen chloride be swept from the reaction mixture prior to the addition of the ammonia gas, thereby reducing the amount of ammonium chloride formed as a result of the addition of ammonia. A sufficient quantity of ammonia, however, should be added to react with substantially all the hydrogen chloride in the reaction mixture. The amount of amide added may vary over a range of from 1.5 to about 5 times the weight of the vanadium oxytrichloride. When the amide is present in a weight ratio of about 1:1 with the vanadium oxytrichloride, the ammonium chloride will not readily separate from the ethyl vanadate. Preferably, the weight ratio of amide to vanadium oxytrichloride is from 1.5:1 to about 5:1 and more preferably from about 2:1 to about 3:1.

The reactants are maintained together at a temperature and for a time sufficient to produce the desired ethyl vanadate. The latitude of the temperature is such that the reaction can be conducted from about 0° up to about 80° C. and more preferably from about 10° C. to about 50° C. The reaction time may range from several minutes up to several hours, e.g., from about 1 to 8 hours. When the reaction is adjusted to operate at optimum conditions, maximum yields of pure product are obtained with minimal degradation.

Although the reaction is normally run at atmospheric pressure, it can be run at sub-atmospheric or super-atmospheric pressures in either a batch or continuous process.

If desired, the ethyl vanadate product may be further purified by distillation or other conventional means. If the ethyl vanadate is to be distilled or if for any other reason it is desired to heat the ethyl vanadate, it is preferred that it be heated under anhydrous conditions.

Moreover, the initial reactants should preferably be completely anhydrous since the presence of moisture causes hydrolysis of the vanadate and consequently results in lower yields. Ideally, an inert gas should blanket the system to prevent decomposition of the product.

The ethyl vanadate of this invention may be used as a catalyst in combination with various aluminum alkyls for the polymerization of olefins to make elastomeric materials.

Various embodiments of this invention are further illustrated by the following examples in which all parts are by weight unless otherwise specified.

EXAMPLE 1

About 282 parts of vanadium oxytrichloride and about 330 parts of hexane are added to a reactor equipped with an agitator and external cooling while sparging with nitrogen. About 158 parts of a mixture containing 170 parts of hexane and 246 parts of ethanol are added to the reactor with agitation and slow nitrogen sparging over a one hour period followed by refluxing for an additional hour. The mixture is cooled to about 50° C. and ammonia is bubbled into the reaction mixture while the remainder of the ethanol-hexane mixture is added dropwise. After two hours the ethanol addition is complete while a positive pressure of ammonia is maintained in the reactor for an additional hour, then 670 parts of formamide are added with agitation. The contents of the reactor are transferred to a separatory funnel where they separate into two phases, an upper phase which is a clear yellow liquid and a lower phase which is the ammonium chloride suspension in the formamide.

The upper phase is separated from the lower phase by decantation and then the solvent is distilled off under vacuum. A product is recovered which is identified as ethyl vanadate having a 99.2 percent purity.

EXAMPLE 2

About 282 parts of vanadium oxytrichloride and about 330 parts of hexane are added to a reactor equipped with an agitator and external cooling means while sparging with nitrogen. About 416 parts of a mixture containing 170 parts of hexane and 246 parts of ethanol are added to the reactor dropwise with agitation and slow nitrogen sparging over a period of about 2 hours. The mixture is cooled to about 50° C. and ammonia is bubbled into the reaction mixture. After about 2 hours, about 670 parts of formamide are added to the reactor with agitation. The contents of the reactor are transferred to a separatory funnel where they separate into two layers, an upper layer containing the ethyl vanadate and a lower layer containing the ammonium chloride suspended in the formamide. The ethyl vanadate recovered from the upper phase has a purity of about 99.2 percent.

EXAMPLE 3

The procedure of Example 2 is repeated except that the amount of formamide was reduced to 282 parts. The resulting slurry does not separate clearly into two liquid layers.

EXAMPLE 4

The procedure of Example 2 is repeated except that toluene is substituted for hexane as the solvent. Ethyl vanadate is recovered having a purity of about 99 percent.

EXAMPLE 5

The procedure of Example 2 is repeated except that benzene is substituted for hexane as a solvent. Ethyl vanadate is recovered having a purity of about 99 percent.

EXAMPLE 6

The procedre of Example 2 is repeated except that dodecane is substituted for hexane as the solvent. Ethyl vanadate having a purity of about 99 percent is obtained.

EXAMPLE 7

The procedure of Example 2 is repeated except that methyl formamide is substituted for the formamide. A phase separation is observed in which the triethyl vanadate is present in the upper hexane layer and the ammonium chloride suspension is present in the methyl formamide layer.

EXAMPLE 8

In a comparison example, about 92 parts of ethanol are added dropwise to a reactor containing about 115 parts of vanadium oxytrichloride with agitation while maintaining the temperature below about 50° C. with external cooling. After about 2 hours, about 540 parts of formamide saturated with ammonia are added to the reactor and agitated for about 1 hour. The reactants are then transferred to a separatory funnel and allowed to stand for 1 hour. No phase separation is observed.

About 300 parts of hexane are added to the separatory funnel, agitated and then allowed to stand for an additional hour. Little, if any, phase separation is observed.

Although specific examples of the invention have been described herein, it is not intended to limit the invention solely thereto, but to include all the variations and modifications falling within the spirit and scope of the appended claims.

The invention claimed is:

1. An improved method for preparing ethyl vanadate by reacting under substantially anhydrous conditions vanadium oxytrichloride with ethanol in a mole ratio of vanadium oxytrichloride to ethanol of from 1:1 to 1:6 and at a temperature of from about 0° to about 80° C in the presence of ammonia, the improvement which comprises conducting the reaction in the presence of an inert hydrocarbon solvent and thereafter adding an amide selected from the class consisting of formamide and methyl formamide in a weight ratio of amide to vanadium oxytrichloriide of at least 1.5:1, said hydrocarbon solvent is immiscible with the amide and is a nonsolvent for the ammonium chloride.

2. The improved method of claim 1 wherein the hydrocarbon solvent is selected from the group consisting of aliphatic and aromatic hydrocarbons.

3. The improved method of claim 2 wherein the hydrocarbon solvent is present in a weight ratio of hydrocarbon solvent to vanadium oxytrichloride of from 1:1 to 5:1.

4. The improved method of claim 1 wherein the amide is present in a weight ratio of amide to vanadium oxytrichloride of from about 2:1 to about 3:1.

5. The improved method of claim 1 wherein an inert gas is passed through the reaction mixture to remove hydrogen chloride prior to the addition of ammonia.

* * * * *